United States Patent [19]

Delledonne et al.

[11] Patent Number: 5,395,949

[45] Date of Patent: Mar. 7, 1995

[54] PROCESS AND CATALYST FOR PREPARING ORGANIC CARBONATES

[75] Inventors: Daniele Delledonne, Oleggio; Franco Rivetti, Milan; Ugo Romano, Vimercate, all of Italy

[73] Assignee: Enichem Synthesis S.p.A., Palermo, Italy

[21] Appl. No.: 1,801

[22] Filed: Jan. 8, 1993

Related U.S. Application Data

[63] Continuation of Ser. No. 718,236, Jun. 20, 1991, abandoned.

[30] Foreign Application Priority Data

Jun. 29, 1990 [IT]  Italy .................... 20809/90
Feb. 13, 1991 [IT]  Italy .................... MI910374

[51] Int. Cl.$^6$ ............... C07D 321/00; C07D 317/08; C07C 69/96
[52] U.S. Cl. ................... 549/228; 549/229; 549/230; 558/260; 558/277
[58] Field of Search ............ 549/228, 229, 230; 558/260, 277

[56] References Cited

U.S. PATENT DOCUMENTS

| | | | |
|---|---|---|---|
| 3,846,468 | 11/1974 | Perrotti et al. | 260/463 |
| 4,187,242 | 2/1980 | Chalk | 528/196 |
| 4,318,862 | 3/1982 | Romano et al. | 260/463 |
| 4,361,519 | 11/1982 | Hallgren | 260/463 |
| 4,604,242 | 8/1986 | Harley et al. | 558/260 |
| 4,636,576 | 1/1987 | Bhattacharya et al. | 558/277 |
| 4,785,130 | 11/1988 | Bhattacharya | 558/277 |

FOREIGN PATENT DOCUMENTS 8707601 12/1987 WIPO .

*Primary Examiner*—Cecilia Tsang
*Attorney, Agent, or Firm*—Philip E. Roux

[57] ABSTRACT

Organic carbonates and cyclic organic carbonates are prepared by reacting an aliphatic or cycloaliphatic alcohol, or, respectively, an aliphatic diol, with carbon monoxide and oxygen, by operating in the presence of a complex catalyst of cobalt with organic ligands bearing one or more oxygen functional groups, as electron donors.

11 Claims, No Drawings

PROCESS AND CATALYST FOR PREPARING ORGANIC CARBONATES

This is a continuation, of application Ser. No. 07/718,236, filed Jun. 20, 1991, now abandoned.

The present invention relates to a catalytic process for preparing organic carbonates.

Organic carbonates are useful intermediates in the chemical sector, and, among these, dimethyl carbonate finds large use in the synthesis of other carbonates, and namely alkyl as well as aryl carbonates (used as plasticizers, synthetic lubricants, monomers for organic glasses, and so forth), in the reactions of methylation and of carbonylation (for preparing urethanes, isocyanates, polycarbonates, and so forth), as an additive for fuels and as an organic solvent.

The classic route to prepare the alkyl carbonates consists in reacting an alcohol with phosgene, such as, e.g., reported in Kirk-Othmer, "Encyclopedia of Chemical Technology", 3rd Ed., No. 4, page 758. Such a process suffers from a number of technical problems, as well as problems relevant to safety, deriving from the use of phosgene.

In order to overcome these drawbacks, alternative synthesis methods were proposed, such as, e.g., the oxidative carbonylation of methanol in the presence of palladium catalysts (U.S. Pat. No. 4,361,519, DE 3,212,535 and 3,212,535, and GB 2,148,881).

The disadvantages of such a process essentially consist in the high cost of the catalyst, in the co-production of oxalic acid esters [see Fenton, J. Org. Chem. 39, 701 (1974)] and in the negative effect of co-produced water which, even at low concentrations, deactivates the catalyst.

Also carbonylation catalysts based on copper were proposed (U.S. Pat. Nos. 3,846,468, 3,952,045, 4,218,391, 4,318,862, 4,360,477, 4,604,242 and 4,785,130), which, unfortunately, show problems deriving from the heterogeneous character of the reaction system and from a certain sensibility to water, which decreases the selectivity of conversion of carbon monoxide into dimethyl carbonate, as well as the reaction rate.

Other processes proposed in the art, which anyway are not very much meaningful from a practical view point, consist in the carbonylation of alcohols in the presence of selenium or mercury compounds, in the reaction of trans-esterification of other carbonates, in the reaction of ureas or urethanes with alcohols, in the presence of catalysts, in the reaction of alkyl halides or sulfates with alkali-metal carbonates, in the reaction of alcohols with carbon dioxide and in the electrochemical synthesis.

The present Applicant found now that dimethyl carbonate and other, also cyclic, organic carbonates, can be prepared in a simple and advantageous way by starting from an aliphatic or cycloaliphatic alcohol, or from an aliphatic diol and carbon monoxide and oxygen, by operating in the presence of particular cobalt compounds as catalysts.

In particular, the present Applicant found that such catalysts make it generally possible the reaction to be carried out in a homogeneous medium, that they are not corrosive, because they normally do not contain halogens, are not very much sensible to water and display characteristics of high activity and selectivity under the typical conditions of oxidative carbonylation.

In accordance therewith, the present invention relates to a process for preparing an organic carbonate:

(I)

wherein:
R is a linear or branched $C_1$–$C_{10}$ alkyl radical; or a $C_5$–$C_8$ cycloalkyl radical;
or a cyclic organic carbonate:

(II)

wherein:
R' is a linear or branched $C_2$–$C_5$ alkylene radical; by means of the reaction of an aliphatic or cycloaliphatic alcohol

R—OH or, respectively, of an aliphatic diol

HO—R'—OH with carbon monixide and oxygen;
said process being characterized in that it is carried out in the presence of a catalyst which is a cobalt salt or cobalt complex with monodentate or polydentate organic anions or ligands, bearing one or more oxygen functional groups as electron donors.

In the catalyst according to the present invention, cobalt preferably is a divalent or trivalent cobalt ion and the organic ligand preferably is an organic carboxylate, beta-diketonate or Schiff base ligand containing an oxygen functional group as the electron donor.

By "Schiff base", the product of condensation of a primary amine with a carbonyl compound, as reported, e.g., by S. Dayagi and Y. Degani in "Methods of Formation of the Carbon-Nitrogen Double Bond" pages 61–130, in "The Chemistry of Functional Groups", Ed. S. Patai. Wiley-Interscience, is meant.

Such a reaction can typically be represented as follows:

$$R^1R^2CO + R^3NH_2 \rightarrow R^1R^2C\!=\!CNR^3 + H_2O$$

wherein $R^1$, $R^2$ and $R^3$ represent organic radicals.

Examples of carboxylate ligands suitable for the intended purpose can be represented by the following formulae:

$$R_1\text{—COO}^-;\ R_2\text{—[COO}^-]_2;\ R_3\text{—[COO}^-]_3;\ R_4\text{—[COO}^-]_4$$

wherein $R_1$, $R_2$, $R_3$ and $R_4$ respectively are monovalent, divalent, trivalent and tetravalent organic radicals containing up to 20 carbon atoms, and which may additionally contain one or more non-carboxy oxygen atoms, nitrogen atoms, sulfur atoms and halogen atoms. Non-limitative examples for such ligands are:

$R_1$—H; $CH_3$—; $CH_3$—$CH_2$—; $CH_3(CH_2)_2$—; $CH_3(CH_2)_3$—; $CH_2$=$CH$—; $(CH_3)_2CH$—; $(CH_3)_2CH$—$CH_2$—;

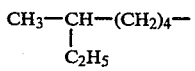

and the radicals: cyclohexyl, phenyl, phenyl substituted with alkyl, aryl, halogen, alkoxy, nitro, or cyano groups;

$R_2 =$ —$CH_2$—, —$CH_2$—$CH_2$—; —CH=CH—; —$CH_2$—$CH_2$—$CH_2$—; —$CH_2$—NH—$CH_2$—$CH_2$—NH—$CH_2$—; —$CH_2$—$(CH_2)_2$—NH—$(CH_2)_2$—$CH_2$—; —$CH_2$—$(CH_2)_2$—$CH_2$—; and —CH(OH)—CH(OH)—, and the radicals: phenylene or substituted phenylene; or $R_2$ is a direct bond;

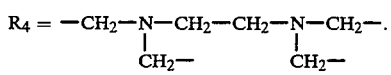

Examples of beta-diketonate ligands suitable for the purpose according to the present invention can be represented by the formula:

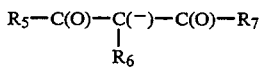

wherein each of $R_5$, $R_6$ and $R_7$ independently represents a hydrogen atom or an aliphatic, cycloaliphatic or aromatic radical of up to 10 carbon atoms, and may additionally contain one or more non-carbonyl oxygen atom(s), nitrogen atom(s), sulfur atom(s) and halogen atom(s). Among beta-diketonates, acetylacetonate radical:

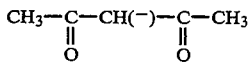

is preferred.

Examples of Schiff base ligands suitable for the purpose according to the present invention are those Schiff bases which are represented by the following formulae:

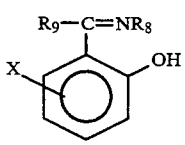

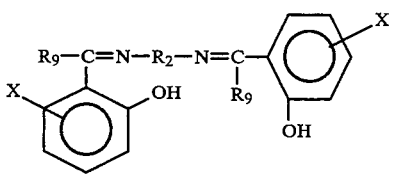

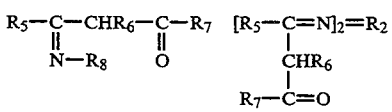

wherein $R_2$, $R_5$, $R_6$ and $R_7$ are as defined above, $R_8$ represents an aliphatic, cycloaliphatic or aromatic radical containing up to 10 carbon atoms, $R_9$ represents the hydrogen atom or has the same meaning as of $R_8$, and X represents an alkyl, aryl, alkoxy, nitro, cyano, amino radical or a halogen atom.

In addition to carboxylate, beta-diketonate or Schiff base ligand and cobalt, the catalyst according to the present invention can additionally contain a monodentate or polydentate nitrogenous ligand, such as, e.g., pyridine, bipyridyl, phenanthroline, tetra-methyl ethylene-diamine and ethylene-diamine, and/or an alkali-metal or alkali-earth metal cation, such as, e.g., sodium and barium.

A particularly active class of catalysts is the class of those complex cobalt catalysts with an organic ligand containing at least one pyridinic ring and bearing one or more oxygen functional groups, as electron donors, definable by means of the following general formula:

P—OH wherein: P represents a radical selected from among those to be defined by the following formulae:

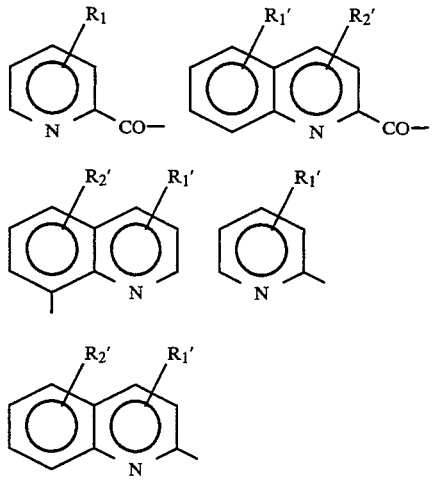

in which formulae $R'_1$ and $R'_2$ represent the hydrogen atom, a halogen atom selected from among chlorine, bromine or iodine, or a $(C_1-C_{20})$-alkyl, $(C_1-C_{20})$-alkoxy, aryl or heteroaryl radical.

Finally, the catalyst can be bonded to a functionalized resin, e.g., through one of the ligands of the coordination sphere.

Specific examples of catalysts useful for the purposes of the present invention are the following: cobalt-(II) acetate $Co(CH_3COO)_2$; cobalt-(III) acetate $Co(CH_3COO)_3$; cobalt-(II) acetylacetonate $Co(acetylacetonate)_2$; cobalt-(III) acetylacetonate $Co(acetylacetonate)_3$; sodium and cobalt-(II) acetylacetonate $Na[Co(acetylacetonate)_3]$; cobalt-(II)-acetylacetonate-bipyridyl $Co(acetylacetonate)_2$-(bipyridyl); Cobalt-(II)-acetylacetonate-phenanthroline $Co(acetylacetonate)_2$-(phenanthroline); sodium-cobalt-(III) ethylenediaminetetraacetate $Na[Co(EDTA)]$; barium-cobalt-(III) ethylenediaminetetraacetate $Ba[Co(EDTA)]_2$; cobalt-(II) citrate $Co_3(citrate)_2$, $[Co(SALEN)]_2.H_2O$, SALEN:
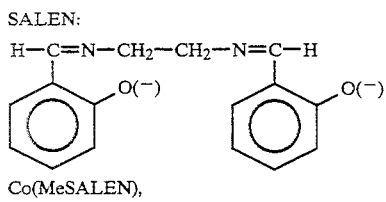
Co(MeSALEN), MeSALEN:
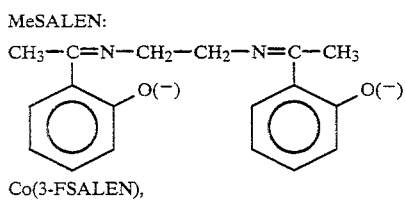
Co(3-FSALEN), 3-FSALEN:
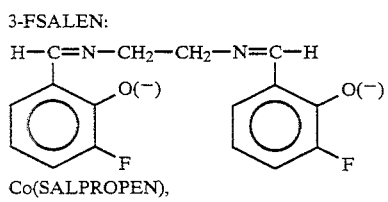
Co(SALPROPEN), SALPROPEN:
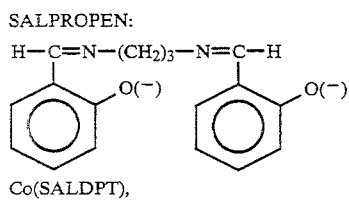
Co(SALDPT), SALDPT:
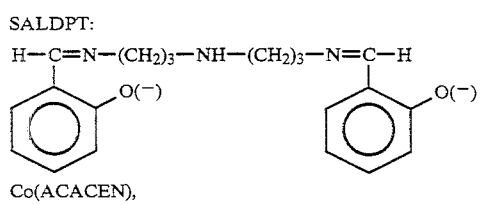
Co(ACACEN), ACACEN:
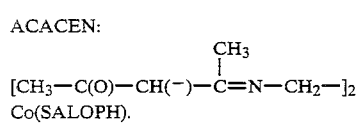
Co(SALOPH).

SALOPH:
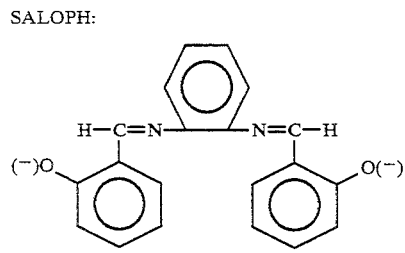

Specific examples of catalysts containing at least one pyridine ring are those which can be defined by means of the following formulae:

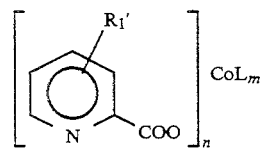

-continued

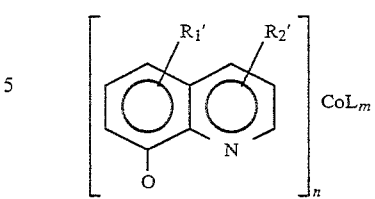

wherein:
n is comprised within the range of from 1 to 3,
m is comprised within the range of from 0 to 5,
$R'_1$ and $R'_2$ have the meaning reported hereinabove, and L represents a secondary ligand selected from the group consisting of either monodentate or polydentate nitrogenous neutral or anionic ligands, and preferably from the group consisting of pyridine, phenanthroline, piperidine, quinoline and isoquinoline, or either monodentate or polydentate oxygen-containing ligands, such as, e.g., $H_2O$, —OH, —$OCH_3$,

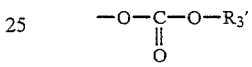

($R'_3 = C_1-C_5$ alkyl), and $CH_3—CO—CH(-)—CO—CH_3$.

Examples of preferred catalysts are:

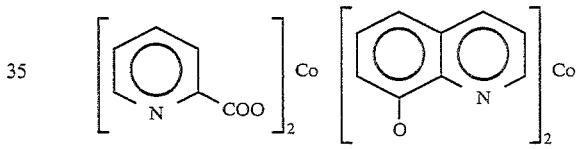

Some of these cobalt complexes are described in the technical literature, in particular by R. H. Bailes et al. in J. Am. Chem. Soc. 69 1947, page 1886, and by M. Calvin in Z. Anal. Ch. 76 1927, page 1911. However, their catalytic activity in the processes of preparation of organic carbonates is not described.

The catalyst can be formed outside of the reaction medium, or it can be formed in situ by starting from a cobalt salt and the selected ligand. The latter can be furthermore used in the stoichiometric amount necessary to form the cobalt complex, or in a larger-than-stoichiometric amount, e.g., in an excess of up to three times as large as the stoichiometric amount.

When in the carbonylation reaction an aliphatic or cycloaliphatic alcohol R—OH is used, the reaction can be schematically shown as follows:

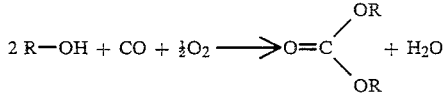

In the preferred form of practical embodiment, R—OH is selected from the group consisting of methanol, ethanol, n-propanol, iso-propanol, n-butanol, iso-butanol, 2-ethyl-hexanol and cyclohexanol, so that in formula (I) R respectively represents methyl, ethyl, n-propyl, iso-propyl, n-butyl, iso-butyl, 2-ethyl-hexyl and cyclohexyl radicals.

In accordance therewith, the organic carbonates (I) which are preferably prepared by means of the process according to the present invention are dimethyl carbonate, diethyl carbonate, di-n-propyl carbonate, di-isopropyl carbonate, di-n-butyl carbonate, di-iso-butyl carbonate, di-2-ethyl-hexyl and dicyclohexyl carbonate.

When an aliphatic diol

is used, the reaction can be schematically shown as follows:

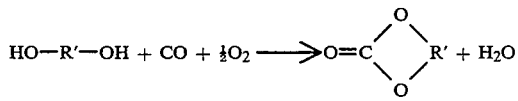

In the preferred form of practical embodiment, the diol HO—R'—OH is ethylene glycol or propylene glycol, and the cyclic carbonate (II) has the formula:

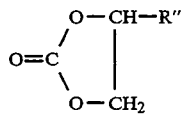

wherein R" respectively is hydrogen or methyl.

In the most preferred form of practical embodiment, the process according to the present invention is used in the preparation of dimethyl carbonate, diethyl carbonate and ethylene carbonate.

In practicing the process according to the present invention, a mixture of the selected alcohol or diol with the previously prepared Co catalyst or with the catalyst precursors, is formed, and said mixture is brought into contact with carbon monoxide and oxygen by operating at temperature and pressure values equal to, or higher than, room values.

More particularly, the process is carried out in the liquid phase, at a temperature comprised within the range of from 25° to 200° C., under a total pressure of carbon monoxide and oxygen comprised within the range of from the atmospheric pressure up to 100 kg/cm$^2$, with a ratio of oxygen partial pressure to carbon monoxide partial pressure comprised within the range of from 0.005:1 to 50:1. Under these conditions, the reaction time will be comprised within the range of from about 1 minute to about 360 minutes.

In the preferred form of practical embodiment, the temperature will be comprised within the range of from 50° to 150° C., the total pressure of oxygen and carbon monoxide will be comprised within the range of from 2 to 100 kg/cm$^2$ and the ratio of the partial pressure of oxygen to the partial pressure of carbon monoxide will be comprised within the range of from 0.01:1 to 0.5:1.

Pure carbon monoxide, or gas mixtures containing carbon monoxide and one or more inert gas(es) can be used. In the same way, pure oxygen, or oxygen diluted with an inert gas, such as nitrogen, e.g., air, or air enriched with oxygen, can be used.

The reaction can be carried out in an inert organic solvent. However, in the preferred form of practical embodiment, the process will be carried out with an excess of the alcohol or diol over the stoichiometric amount; with said excess performing the task of reaction solvent, with a catalyst concentration in the liquid reaction medium comprised within the range of from $10^{-3}$ to 2 mol/liter.

By operating under the hereinabove set forth conditions, the organic carbonate is obtained with high yield and selectivity values, and with good productivity values. The so produced organic carbonate can be separated from the reaction mixture (after the preliminary removal of unreacted carbon monoxide and oxygen), by such normal separation techniques as distillation and fractionation.

The process according to the present invention can be carried out batchwise, as well as in continuous mode.

The following experimental examples are provided in order to illustrate the invention in greater detail.

EXAMPLE 1

50 g of methanol and 2.48 g (10 mmol) of cobalt acetate tetrahydrate Co(CH$_3$COO)$_2$.4H$_2$O are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 100° C., and is kept at said temperature for 2.5 hours, always with stirring. The autoclave is then cooled down to room temperature, the gas is vented and the liquid phase is submitted to gas-chromatographic analysis.

A yield of 2.16 g (24 mmol) of dimethyl carbonate is determined.

EXAMPLE 2

50 g of methanol and 2.57 g (10 mmol) of Co(acetylacetonate)$_2$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 100° C., and is kept at said temperature for 3 hours and minutes always with stirring. The autoclave is then cooled down to room temperature, the gas is vented and the liquid phase is submitted to gas-chromatographic analysis.

A yield of 2.61 g (29 mmol) of dimethyl carbonate is determined.

EXAMPLE 3

50 g of methanol, 2.48 g (10 mmol) of cobalt acetate tetrahydrate Co(CH$_3$COO)$_2$.4H$_2$O and 1.64 g (20 mmol) of sodium acetate CH$_3$COONa are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 100° C., and is kept at said temperature for 5 hours, always with stirring. The autoclave is then cooled down to room temperature, the gas is vented and the liquid phase is submitted to gas-chromatographic analysis.

A yield of 2.97 g (33 mmol) of dimethyl carbonate is determined.

EXAMPLE 4

50 g of methanol, 3.27 g (10 mmol) of cobalt bromide hexahydrate $CoBr_2.6H_2O$ and 1.64 g (20 mmol) of sodium acetate $CH_3COONa$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 100° C., and is kept at said temperature for 4.5 hours, always with stirring. The autoclave is then cooled down to room temperature, the gas is vented and the liquid phase is submitted to gas-chromatographic analysis.

A yield of 1.17 g (13 mmol) of dimethyl carbonate is determined.

EXAMPLE 5

50 g of methanol, 2.38 g (10 mmol) of cobalt chloride hexahydrate $CoCl_2.6H_2O$ and 1.64 g (20 mmol) of sodium acetate $CH_3COONa$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 107° C., and is kept at said temperature for 4 hours, always with stirring. The autoclave is then cooled down to room temperature, the gas is vented and the liquid phase is submitted to gas-chromatographic analysis.

A yield of 0.828 g (9.2 mmol) of dimethyl carbonate is determined.

EXAMPLE 6

50 g of methanol and 1.77 g (10 mmol) of anhydrous cobalt acetate $Co(CH_3COO)_2$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 130° C., and is kept at said temperature for 2 hours and 50 minutes, always with stirring. The autoclave is then cooled down to room temperature, the gas is vented and the liquid phase is submitted to gas-chromatographic analysis.

A yield of 4.05 g (45 mmol) of dimethyl carbonate is determined.

EXAMPLE 7

50 g of methanol and 3.79 g (10 mmol) of $Na[Co(acetylacetonate)_3]$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 130° C., and is kept at said temperature for 90 minutes, always with stirring. The autoclave is then cooled down to room temperature, the gas is vented and the liquid phase is submitted to gas-chromatographic analysis.

A yield of 2.34 g (26 mmol) of dimethyl carbonate is determined.

EXAMPLE 8

50 g of methanol and 2.06 g (5 mmol) of $Co(acetylacetonate)_2.(bipyridyl)$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 100° C., and is kept at said temperature for 180 minutes, always with stirring. The autoclave is then cooled down to room temperature, the gas is vented and the liquid phase is submitted to gas-chromatographic analysis.

A yield of 4.50 g (50 mmol) of dimethyl carbonate is determined.

EXAMPLE 9

50 g of methanol and 3.55 g (10 mmol) of $Co(acetylacetonate)_3$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 100° C., and is kept at said temperature for 120 minutes, always with stirring. The autoclave is then cooled down to room temperature, the gas is vented and the liquid phase is submitted to gas-chromatographic analysis.

A yield of 1.485 g (16.5 mmol) of dimethyl carbonate is determined.

EXAMPLE 10

50 g of ethylene glycol and 1.77 g (10 mmol) of anhydrous cobalt acetate $Co(CH_3COO)_2$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 100° C., and is kept at said temperature for 120 minutes, always with stirring. The autoclave is then cooled down to room temperature, the gas is vented and the liquid phase is submitted to gas-chromatographic analysis.

A yield of 1.50 g (17 mmol) of ethylene carbonate is determined.

EXAMPLE 11

50 g of anhydrous ethanol and 2.06 g (5 mmol) of $Co(acetylacetonate)_2.(bipyridyl)$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 $kg/cm^2$ and 10 $kg/cm^2$. With stirring, the autoclave is heated up to 100° C., and is kept at said temperature for 4 hours, always with stirring. The autoclave is then cooled down to room temperature, the gas is vented and the liquid phase is submitted to gas-chromatographic analysis.

A yield of 4.37 g (37 mmol) of diethyl carbonate is determined.

EXAMPLE 12

100 g of methanol and 3.33 g (5 mmol) of [Co(-SALEN)]$_2$.H$_2$O are charged to an autoclave of 500 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 120° C., and is kept at said temperature for 90 minutes, always with stirring. The autoclave is then cooled down to room temperature, the gas is vented and the liquid phase is submitted to gas-chromatographic analysis.

A yield of 28.8 g (320 mmol) of dimethyl carbonate is determined.

EXAMPLE 13

100 g of methanol, 2.06 g (5 mmol) of Co(acetylacetonate)$_2$.(bipyridyl) and 15 g of trimethyl orthoformate are charged to an autoclave of 500 ml of capacity with an internal lining of Teflon ® and equipped with mechanical stirring means and heat exchange means.

To the autoclave, carbon monoxide and oxygen are charged, up to their partial pressures respectively of 20 kg/cm$^2$ and 10 kg/cm$^2$. With stirring, the autoclave is heated up to 100° C., and is kept at said temperature for 240 minutes, always with stirring. The autoclave is then cooled down to room temperature, the gas is vented and the liquid phase is submitted to gas-chromatographic analysis.

A yield of 7.2 g (80 mmol) of diethyl carbonate is determined.

EXAMPLE 14

50 g of anhydrous methanol and 3.1 g (10 mmol) of Co(SALPROPEN) are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 110° C., and is kept at said temperature for 4 hours, always with stirring. The autoclave is then cooled down to room temperature, the gas is vented and the liquid phase is submitted to gas-chromatographic analysis.

A yield of 9.0 g (100 mmol) of dimethyl carbonate is determined.

EXAMPLE 15

50 g of anhydrous methanol and 0.65 g (2.3 mmol) of Co(ACACEN) are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 110° C., and is kept at said temperature for 4 hours, always with stirring. The autoclave is then cooled down to room temperature, the gas is vented and the liquid phase is submitted to gas-chromatographic analysis.

A yield of 1.06 g (12 mmol) of dimethyl carbonate is determined.

EXAMPLE 16

50 g of anhydrous methanol and 2.33 g (10 mmol) of Co(ibutyrate)$_2$ are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 120° C., and is kept at said temperature for 4 hours, always with stirring. The autoclave is then cooled down to room temperature, the gas is vented and the liquid phase is submitted to gas-chromatographic analysis.

A yield of 1.8 g (20 mmol) of dimethyl carbonate is determined.

EXAMPLE 17

158 g of methanol and 4.80 g (12.8 mmol) of the complex catalyst cobalt bis(picolinate) tetrahydrate:

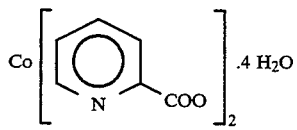

are charged to a steel autoclave of 250 ml of capacity with an internal lining of Teflon ® and equipped with mechanical stirring means and heat exchange means.

To the autoclave, carbon monoxide and oxygen are charged, up to partial pressures respectively of 15 kg/cm$^2$ and 5 kg/cm$^2$. With stirring, the autoclave is heated up to 120° C., and is kept at said temperature for 5 hours, always with stirring. The autoclave is then cooled down to room temperature, the gas is vented and the liquid phase is submitted to gas-chromatographic analysis.

A yield of 15.49 g (172 mmol) of dimethyl carbonate is determined.

The reaction liquid is evaporated by means of one of conventional methods, and the catalyst is recycled to the reaction. The operation is repeated a plurality of times, with no loss of activity being suffered by the cobalt complex catalyst, as demonstrated by the following data:

| No. of catalyst recycle | mmol (g) of produced dimethyl carbonate |
| --- | --- |
| 1 | 230 (20.7) |
| 2 | 180 (16.21) |
| 3 | 252 (22.69) |
| 4 | 240 (21.58) |
| 5 | 240 (21.58) |
| 6 | 244 (21.03) |
| 7 | 240 (21.57) |

EXAMPLE 18

150 ml of anhydrous methanol and 3.33 g (9.4 mmol) of Co(MeSALEN) are charged to an autoclave of 250 ml of capacity with an internal lining of Teflon ® and equipped with mechanical stirring means and heat exchange means.

To the autoclave, carbon monoxide and oxygen are charged, up to partial pressures respectively of 20 kg/cm$^2$ and 10 kg/cm$^2$. With stirring, the autoclave is heated up to 120° C., and is kept at said temperature for 5 hours, always with stirring. The autoclave is then cooled down to room temperature, the gas is vented and the liquid phase is submitted to gas-chromatographic analysis.

A yield of 19.9 g (221 mmol) of dimethyl carbonate is determined.

We claim:

1. A process for preparing an organic carbonate:

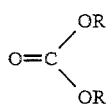

wherein R is a linear or branched $C_1$–$C_{10}$ alkyl radical, or a $C_5$–$C_8$ cycloalkyl radical;
or a cyclic organic carbonate:

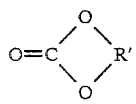

wherein R' is a linear or branched $C_2$–$C_5$ alkylene radical; by reacting an aliphatic or cycloaliphatic alcohol

or, respectively, an aliphatic diol

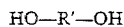

with carbon monoxide and oxygen;
wherein said process is carried out in the presence of a catalyst comprising a divalent or trivalent cobalt ion and an organic ligand selected from the group consisting of:

(i) a carboxylate ligand having the formula:

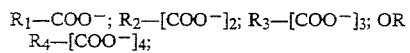

wherein $R_1$, $R_2$, $R_3$ and $R_4$ are independently selected from the group consisting of monovalent, divalent, trivalent and tetravelent radicals having up to 20 carbon atoms, and monovalent, divalent, trivalent and tetravalent organic radicals having up to 20 carbon atoms which additionally contain non-carbonyl oxygen atom(s), nitrogen atom(s), sulfur atom(s) and halogen atom(s), (ii) a beta-diketonate ligand having the formula:

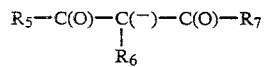

wherein each of $R_5$, $R_6$ and $R_7$ independently is selected from the group consisting of a hydrogen atom, aliphatic, cycloaliphatic and aromatic radicals having up to 10 carbon atoms, and aliphatic cycloaliphatic and aromatic radicals having up to 10 carbon atoms which additionally contain non-carbonyl oxygen atom(s), nitrogen atom(s), sulfur atom(s) and halogen atom(s), (iii) a Schiff base having one or more oxygen functional groups selected from the group consisting of:

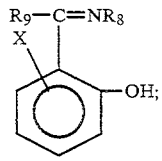

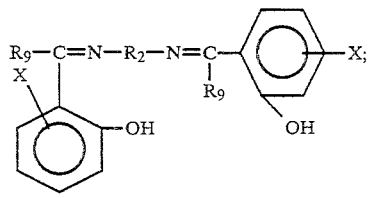

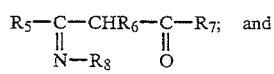

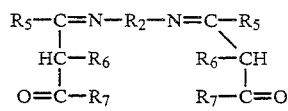

wherein $R_2$, $R_5$ and $R_7$ are as above defined, $R_8$ is an aliphatic, cycloaliphatic or aromatic radical having up to 10 carbon atoms, $R_9$ is a hydrogen atom or is the same as $R_8$, and X is an alkyl, alkoxy, nitro, cyano, amino radical, or a halogen atom; and (iv) a ligand having the formula:

wherein P is selected from those having the formula:

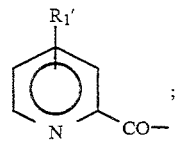

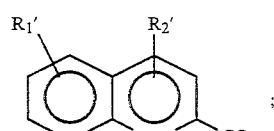

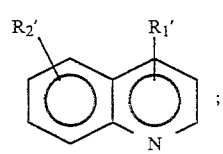

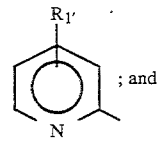

-continued

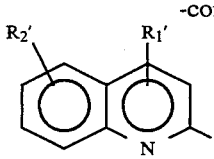

in which formulae R'₁ and R'₂ are a hydrogen atom, a halogen atom selected from the group consisting of chlorine, bromine or iodine, a $(C_1-C_{20})$alkyl, or a $(C_1-C_{20})$ alkoxy radical.

2. A process according to claim 1 wherein in said carboxylate ligands (i):

R₁ is selected from H; CH₃—; CH₃—CH₂; CH₃(CH₂)₂—; CH₃(CH₂)₃; CH₂=CH—; (CH₃)₂CH—; (CH₃)₂CH—CH₂—;

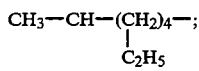

a cyclohexyl radical; a phenyl radical; a phenyl radical substituted with an alkyl, halogen, alkoxy, nitro or cyano group;

R₂ is selected from —CH₂; —CH₂—CH₂—; —CH=CH—; —CH₂—CH₂—CH₂—; CH₂—NH—CH₂—CH₂—NH—CH₂—; —CH₂—(CH₂)₂—NH—(CH₂)₂—CH₂—; —CH₂—(CH₂)₂—CH₂—; —CH(OH)—CH(OH)—; a phenylene radical; or a direct bond;

R₃ is selected from —CH₂—C(OH)—CH₂—; and

R₄ is selected from

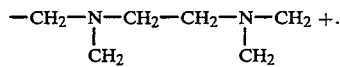

3. A process according to claim 1, wherein said beta-diketonate ligand (ii) is

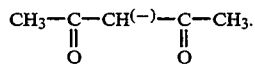

4. A process according to claim 1, wherein said catalyst additionally contains a nitrogen ligand selected from the group consisting of pyridine, bipyridil, phenanthroline, tetra-methyl ethylene-diamine, and an alkali or alkali-earth cation selected from the group consisting of sodium and barium.

5. A process according to claim 1, wherein said catalyst is selected from the group consisting of:

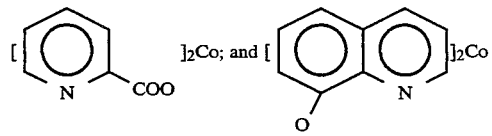

6. A process according to claim 1, wherein said aliphatic alcohol is selected from the group consisting of methanol, ethanol, n-propanol, iso-propanol, n-butanol, iso-butanol, 2-ethyl-hexanol and cyclohexanol, and the aliphatic diol is selected from the group consisting of ethylene glycol and propylene glycol.

7. A process according to claim 1, wherein said aliphatic alcohol is methanol, ethanol, and said aliphatic diol is ethylene glycol.

8. A process according to claim 1, wherein said process is carried out in the liquid phase, at a temperature of 25° to 200° C., under a carbon monoxide and oxygen total pressure of from atmospheric pressure up to 100 kg/cm², with an oxygen to carbon monoxide partial response ratio of 0.005:1 to 50:1, and a reaction time of 1 to about 360 microns.

9. A process according to claim 1, wherein said temperature is in the range of from 50° to 150° C., said total pressure is in the range of from 2 to 100 kg/cm², and said oxygen to carbon monoxide partial pressure ratio is in the range of from 0.01:1 to 0.5:1.

10. A process according to claim 1, wherein said process is carried out with the alcohol or diol being in excess over the stoichiometric amount, and with a catalyst concentration in the liquid reaction medium in the range of from $10^{-3}$ to 2 mol/liter.

11. A process according to claim 1, wherein said catalyst is selected from the group consisting of: Co(CH₃COO)₂; Co(CH₃COO)₃; Co(acetylacetonate)₂; Na; Co(acetylacetonate)₂ (bipyridil); Co(acetylacetonate)₂ (phenatroline); Na; Ba₂; Co(citrate)₂; 2.H₂O; Co(MeSALEN); Co(3-FSALEN), Co(SALPROPEN); Co(SALDPT); Co(ACACEN), Co(SALOPH),

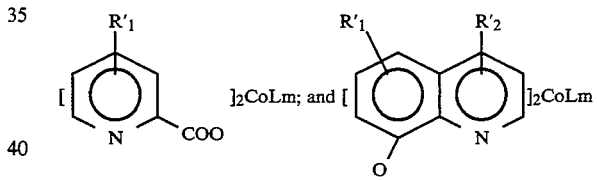

wherein:
n is 1 to 3,
m is 0 to 5,
R'₁ and R'₂ are as above defined, and
L is a secondary ligand selected from the group consisting of pyridine, phenanthroline, piperidine, quinoline, isoquinoline, H₂O, —OH, —OCH₃,

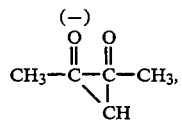

and 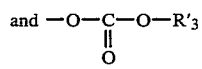

wherein R'₃ is a $C_1-C_5$ alkyl.

* * * * *

UNITED STATES PATENT AND TRADEMARK OFFICE
CERTIFICATE OF CORRECTION

PATENT NO. : 5,395,949
DATED : March 7, 1995
INVENTOR(S) : Daniele Delledonne, Franco Rivetti and Ugo Romano It is certified that error appears in the above-indentified patent and that said Letters Patent is hereby corrected as shown below:

Col. 15,
In Claim 2, line 35, in the formula delete "+" and insert -- - --.

Col. 16,
In Claim 11, line 38, in both occurences delete "$_2CoLm$" and insert --$_nCoL_m$--.

Signed and Sealed this

Twenty-third Day of July, 1996

Attest:

BRUCE LEHMAN

*Attesting Officer*      *Commissioner of Patents and Trademarks*